(12) United States Patent
Wang et al.

(10) Patent No.: US 7,420,681 B1
(45) Date of Patent: Sep. 2, 2008

(54) GAS PURGE SYSTEM AND METHODS

(75) Inventors: Ning-Yi Wang, Fremont, CA (US);
Ching-Ling Meng, Sunnyvale, CA (US); Anthony Tang, San Jose, CA (US)

(73) Assignee: KLA Tencor Technologies Corporation, Milpitas, CA (US)

( * ) Notice: Subject to any disclaimer, the term of this patent is extended or adjusted under 35 U.S.C. 154(b) by 235 days.

(21) Appl. No.: 11/457,524

(22) Filed: Jul. 14, 2006

(51) Int. Cl.
*G01N 21/00* (2006.01)
*G01J 4/00* (2006.01)

(52) U.S. Cl. ........................ 356/437; 356/369
(58) Field of Classification Search ................ 356/437, 356/364, 369
See application file for complete search history.

(56) References Cited

U.S. PATENT DOCUMENTS

| | | | | |
|---|---|---|---|---|
| 5,835,221 | A * | 11/1998 | Lee et al. | 356/369 |
| 6,151,116 | A * | 11/2000 | Hirosawa | 356/369 |
| 6,222,199 | B1 | 4/2001 | Freeouf | 250/559.27 |
| 6,275,288 | B1 * | 8/2001 | Atkinson et al. | 356/246 |
| 6,813,026 | B2 * | 11/2004 | McAninch | 356/445 |
| 2002/0149774 | A1 * | 10/2002 | McAninch | 356/445 |
| 2004/0150820 | A1 | 8/2004 | Nikoonahad et al. | 356/364 |

\* cited by examiner

*Primary Examiner*—Roy M Punnoose
(74) *Attorney, Agent, or Firm*—Joshua D. Isenberg; JDI Patent (57) ABSTRACT

Gas purge systems and methods and a spectroscopic ellipsometer are disclosed. A purge gas system may include an input beam optics housing, a collection optics housing and a gas purge manifold. The input beam optics housing may include a first gas flow path between a first gas inlet and an aperture in a first nose cone proximate a measurement position. The collection optics housing may include a second gas flow path between a second gas inlet and an aperture in a second nose cone proximate the measurement position. The gas purge manifold may be disposed between the input beam optics housing and the collection optics housing. The gas purge manifold has a third gas flow path between a third gas inlet and an aperture in the gas manifold proximate the measurement position. The ellipsometer may include input beam optics in the input beam optics housing and collection optics in the collection optics housing. First, second, and third flows of purge gas may be supplied through the input beam optics housing, collection optics housing and gas purge manifold respectively. The purge gas is delivered directly to a measurement position of a surface of a substrate through the gas purge manifold, the first nosecone and the second nose cone.

29 Claims, 6 Drawing Sheets

GAS PURGE SYSTEM AND METHODS

FIELD OF THE INVENTION

This invention generally relates to optical metrology devices. More specifically, the invention relates to an optical instrument that includes a gas-flow system for the purpose of purging to remove oxygen from the vacuum UV beam path.

BACKGROUND OF THE INVENTION

Ellipsometry is a versatile optical technique that has applications in many different fields, from the microelectronics to semiconductor industries (for characterizing oxides or photoresists on silicon wafers, for example) to biology. This very sensitive measurement technique provides unequalled capabilities for thin film metrology. As an optical technique, spectroscopic ellipsometry is nondestructive and uses polarized light to probe the dielectric properties of a sample. An ellipsometer is a type of spectrometer that measure changes in the ellipticity of polarized light upon reflection from a surface. Changes in ellipticity of an incident beam polarized light can provide information regarding properties of thin films.

The semiconductor industry is presently developing photolithographic methods utilizing 157 nm wavelength laser light as the next step in the continuing reduction of device length scales. These wavelengths lie within a region known as the vacuum ultraviolet (VUV), in which the high absorption coefficients of oxygen lower the attenuation length in standard air to fraction of a millimeter. In particular, UV light with wavelengths less than about 180 nm may be strongly absored in air due to the presence of oxygen and/or water vapor. Achieving the transmission and stability necessary for a VUV optical metrology tool, in which the optical paths are about 0.5-2 m, therefore requires oxygen concentration in the low parts-per-million (ppm) range averaged over the optical paths. A major engineering challenge in the development of optical metrology is simultaneously providing high wafer through-put and low optical absorption. Nitrogen purge chambers may be used in conjunction with VUV Spectroscopic Ellipsometer (SE) systems to reduce levels of oxygen and/or water vapor in the optical beam paths.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Figure 1A:
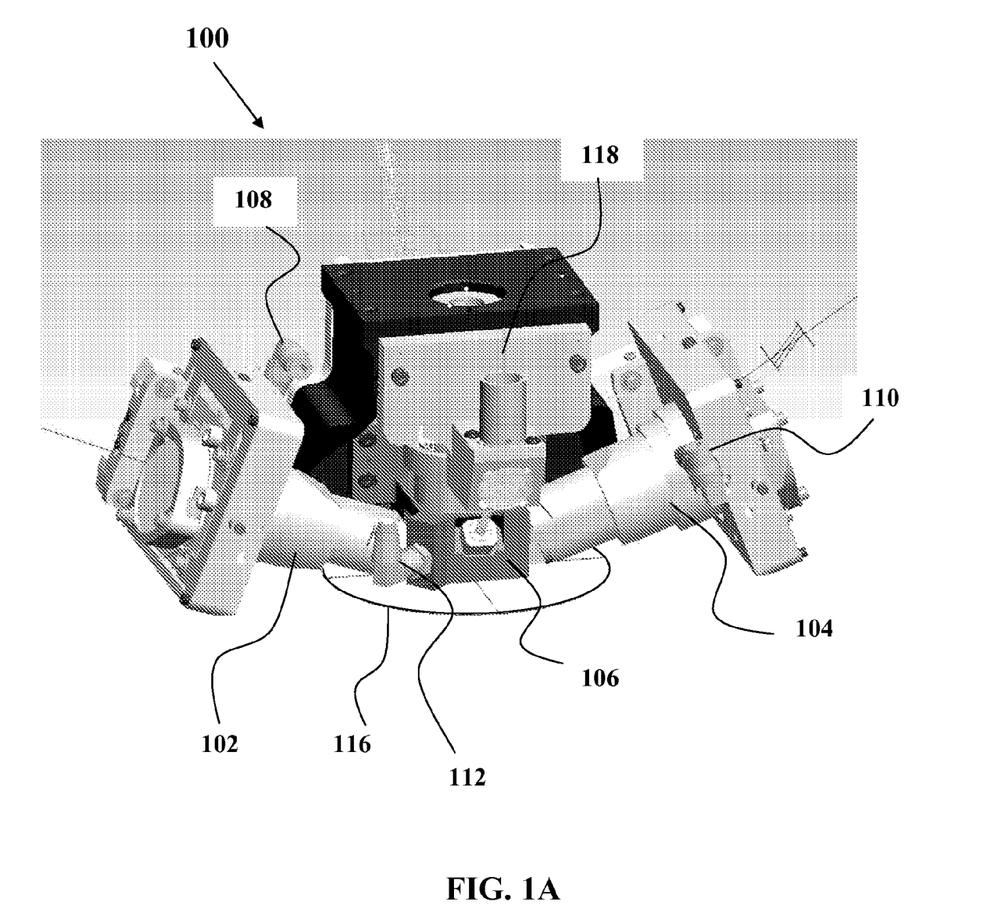
FIG. 1A is a front perspective view of a gas purge system according to an embodiment of the present invention.

FIGS. 1A-1D illustrate a gas purge system 100 according to embodiments of the present invention. As shown in FIG. 1A, the gas purge system 100 may include an input beam optics housing 102, a collection optics housing 104 and a gas purge manifold 106. The gas purge system 100 also includes first, second and third gas inlets 108, 110 and 112, respectively. The first gas inlet 108 is located on input beam optics housing 102. The second gas inlet 110 is located on the collection optics housing 104. The third gas inlet 112 is located on the gas purge manifold 106. As shown in FIG. 1A, a target substrate 116 may be positioned under the gas purge manifold 106 for optical measurement with an optical system used in conjunction with the gas purge system 100.

Figure 1B:
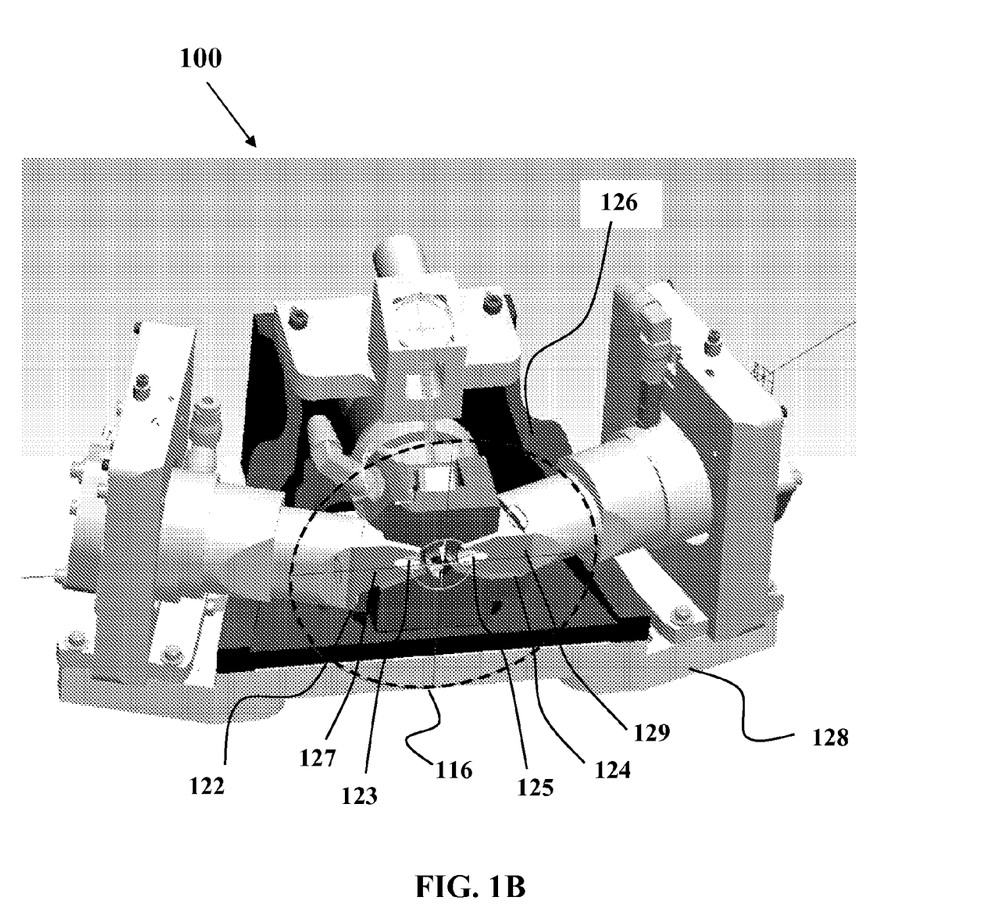
FIG. 1B is a bottom perspective view of the gas purge system according to an embodiment of the present invention.

FIG. 1B illustrates a bottom perspective view of the gas purge system 100 of the present invention. In FIG. 1B, the input beam optics housing 102 includes a first nosecone 122. The collection optics housing 104 includes a second nosecone 124. The nosecones 122 and 124 may have truncated shapes. Specifically, each nosecone 122, 124 may include truncated sections having substantially flat surfaces 127, 129 oriented more or less parallel to the substrate 116 to be analyzed by the BBSE system used with the purge gas system 100. Portions of the optics housings 102, 104 may also be truncated in a similar manner. The truncated portions allow the substrate 116 to be positioned The gas purge system 100 also includes an objective mount 126 for mounting the objective lens 114 and a dovetail 128 to mount the BBSE focus mirrors housing 102 and BBSE collection mirrors housing 104. The purge gas manifold 106 may optionally be adapted to include auxiliary optical components, e.g., a focus lens 138 and a collection lens 140 located inside the gas purge manifold 106, which are shown in FIG. 1D.

The input beam optics housing 102 includes a passage $P_1$ between the first gas inlet 108 and a first aperture 123 proximate a measurement point 103. The passage $P_1$ may allow purge gas to bypass optical components in the housing 102, e.g., lenses and the like. The collection optics housing 104 includes a passage $P_2$ between the second gas inlet 110 and a second aperture 125 proximate a measurement point 103. The measurement position 103 may be located at an intersection of an optical path 132 for the input beam optics, an optical path 133 for the collection optics and a surface of the substrate 116. The nosecones 122, 124 may provide part of the passages $P_1$, $P_2$ for flows of purge gas from the gas inlets 108, 110 to exit apertures 123, 125.

The gas purge manifold 106 may supply a purge gas flow pattern from between optics modules, such as the input beam optics housing 102 and the collection optics housing 104, and directed toward the substrate 116, particularly at and around the measurement position 103. The purge manifold 106 includes a third passage $P_3$ for flow of purge gas between the third gas inlet 112 and a third aperture 113 located in the purge gas manifold 106 proximate the surface of the substrate 116.

Inside an optical instrument used in conjunction with the purge gas system 100, e.g., a broad-band spectroscopic ellipsometer (BBSE), purge gas may be purged along the optical paths 132, 133. Any suitable purge gas may be used in the system 100. Examples of suitable purges gases include, but are not limited to, nitrogen, argon and helium. Purge gas may be supplied through, e.g., through standard gas fittings located at the inlets 108, 110 and 112 and may be delivered directly to the measurement position 103 through the purge gas manifold 106 and two nosecones 122 and 124. As may be seen from FIG. 1C, the purge gas flow through each nosecone 122 or 124 may be directed at an oblique angle to the surface of the substrate 116 more or less parallel to the light paths 132, 133. Purge gas flow from the gas purge manifold 106 may be normal to the surface of the substrate 116.

Figure 1C:
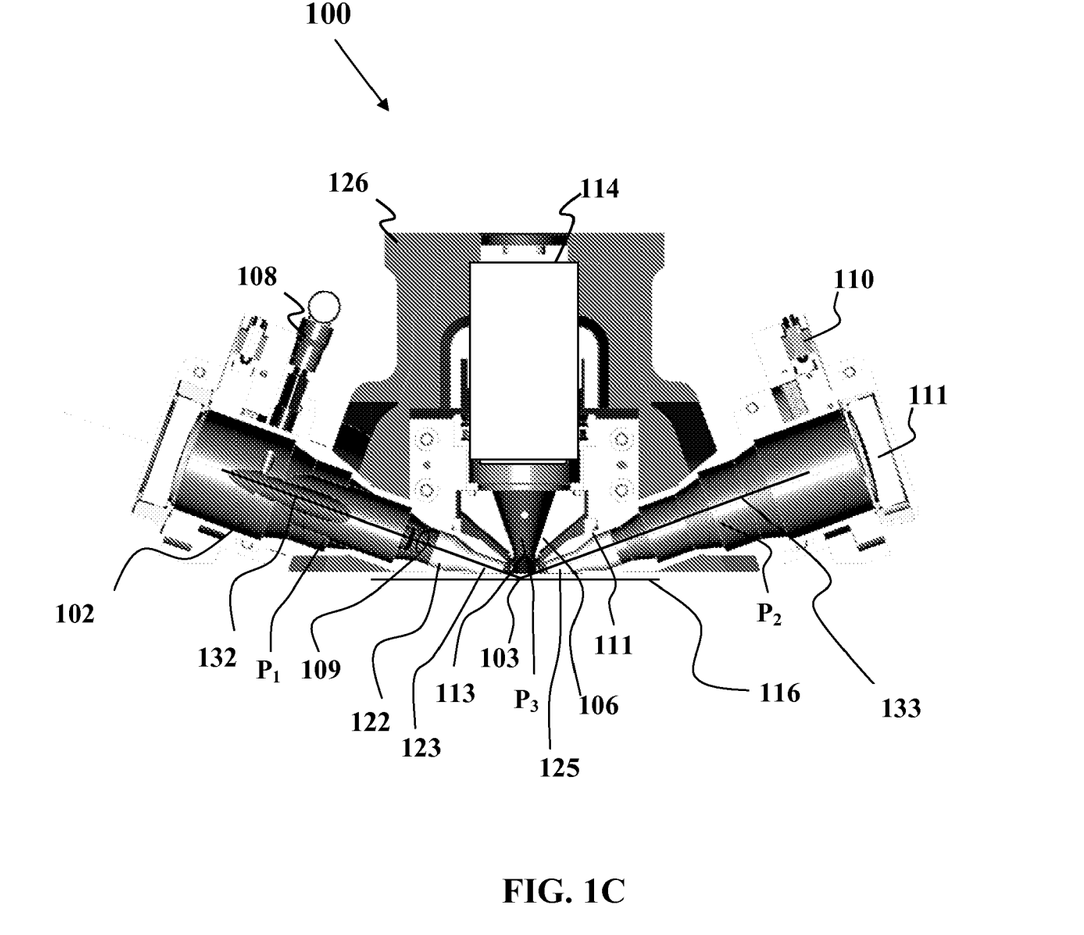
FIG. 1C is a cross section view in a light path plane of the gas purge system of FIGS. 1A-1B.
Figure 1D:
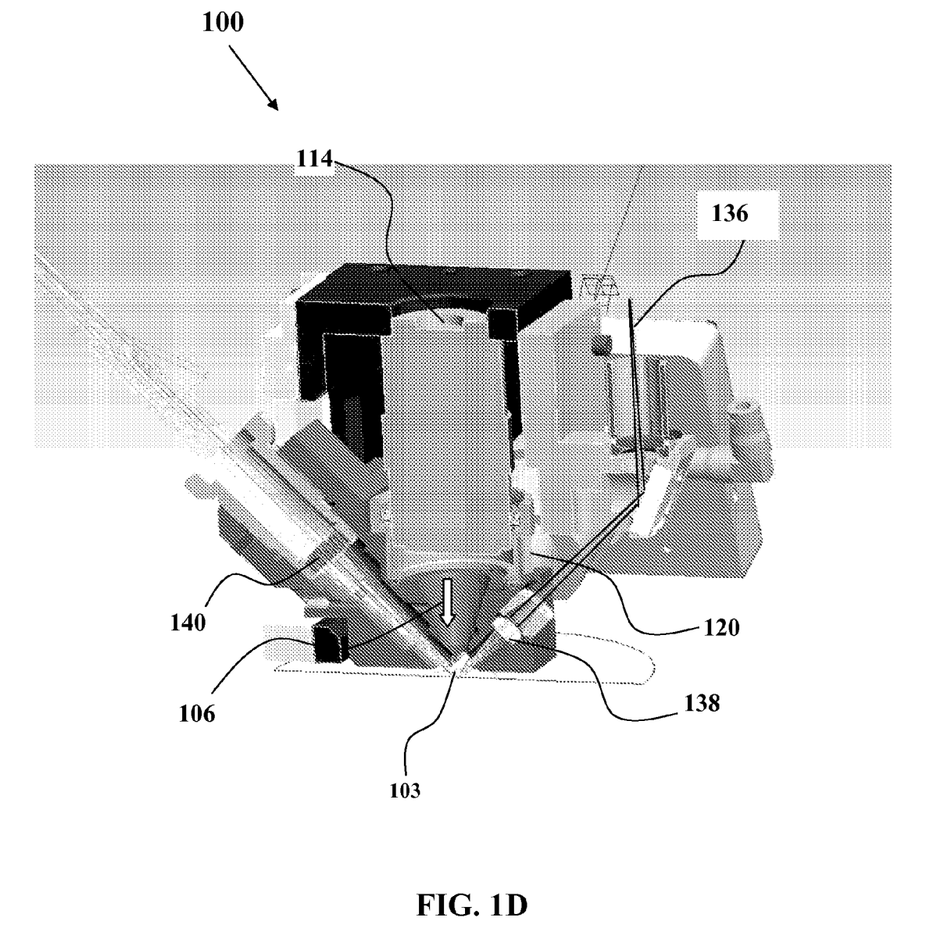
FIG. 1D is a cross section view in Auto-focus light path plane the gas purge system according to an embodiment of the present invention.

As shown in FIGS. 1C-1D, components of the purge gas system 100 may provide one or more optical paths for an optical system used in conjunction with the gas purge system 100. For example, as discussed above, input beam optical path 132 (or portions thereof) may be located within the input beam optics housing 102. Similarly, the collection optical path 133 (or portions thereof) may be located in the collection optics housing 104. Furthermore, the gas purge manifold 106 (or portions thereof) may provide optical paths (or portions thereof) for light to and/or from other optical components. For example, an upper portion of the gas purge manifold 106 may be sized and shaped to receive an objective lens 114. An objective sleeve 120 may provide a gas tight seal between the objective lens 114 and the purge gas manifold 106. The objective lens may be fixed in position during operation of the gas purge system 100 by an objective mount. The objective sleeve 120 may move up and down during the installation and removal of the objective lens 114. As shown in FIG. 1D, in addition to the nitrogen purge function, the purge gas manifold 106 may also provide a light path 136 that bypasses the objective lens 114. The light path 136 may be used for an auxiliary optical system, e.g., an auto focus system. Focus and/or collection lenses 138/140 for the auxiliary optical system may be packaged inside the purge gas manifold 106.

The gas purge system 100 may be used in conjunction with any suitable optical system. By way of example, the optical system may be a spectroscopic ellipsometer system. Such a system may generally include an input beam optical column disposed within the input beam optics housing 102 and collection optics disposed within the collection optics housing 104. The input beam optical column may include optical components 109, such as lenses, mirrors and the like, that guide light from a remote source towards a measurement position 103 on the target substrate 116. The collection optics may include optical components 111, e.g., lenses, mirrors, diffraction gratings and other optical elements that collect and analyze light from the measurement position 103. By way of example, the gas purge system 100 may be used with a Broad-Band Spectroscopic Ellipsometer (BBSE) system from KLA-Tencor of San Jose, Calif. Alternatively, the gas purge system 100 may be used with other optical systems such as reflectometers, and the like.

Due to the relatively small volume of the purge gas chamber 105 and high flow rate, the overall response time of nitrogen purge may be relatively fast. The passages $P_1$, $P_2$ and $P_3$ and proximity of the apertures 113, 123, 125 and truncated shape of the nosecones 122 and 124 allow purge gas to be delivered quickly and directly to the measuring position 103. As a result, a BBSE used in conjunction with the purge gas system 100 may quickly establish a signal. For example, an initial purge to remove moisture may take about one hour. After such a purge, an optical system that uses the purge gas system 100 can recover an optical signal in less than one minute from a sustaining mode. As used herein, the term "sustaining mode" generally refers to a condition of reduced flow of purge gas subsequent to an initial purge. By way of example, the sustaining mode may be used during periods in which the optical system is idle. Flow of purge gas during operation of the optical system is generally greater than the purge gas flow during the sustaining mode and is generally less than the purge gas flow during an initial purge.

Figure 2:
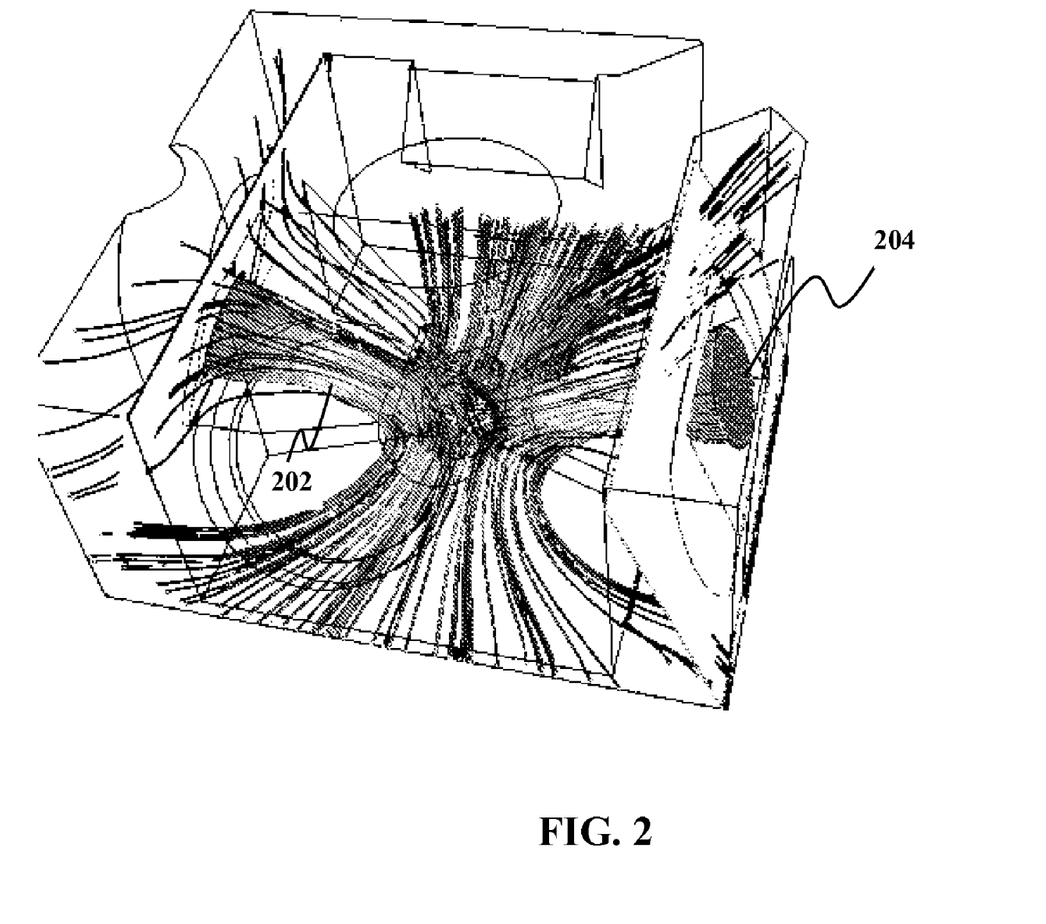
FIG. 2 illustrates a first flow pattern of the Nitrogen in a part of the gas purge system.
Figure 3:
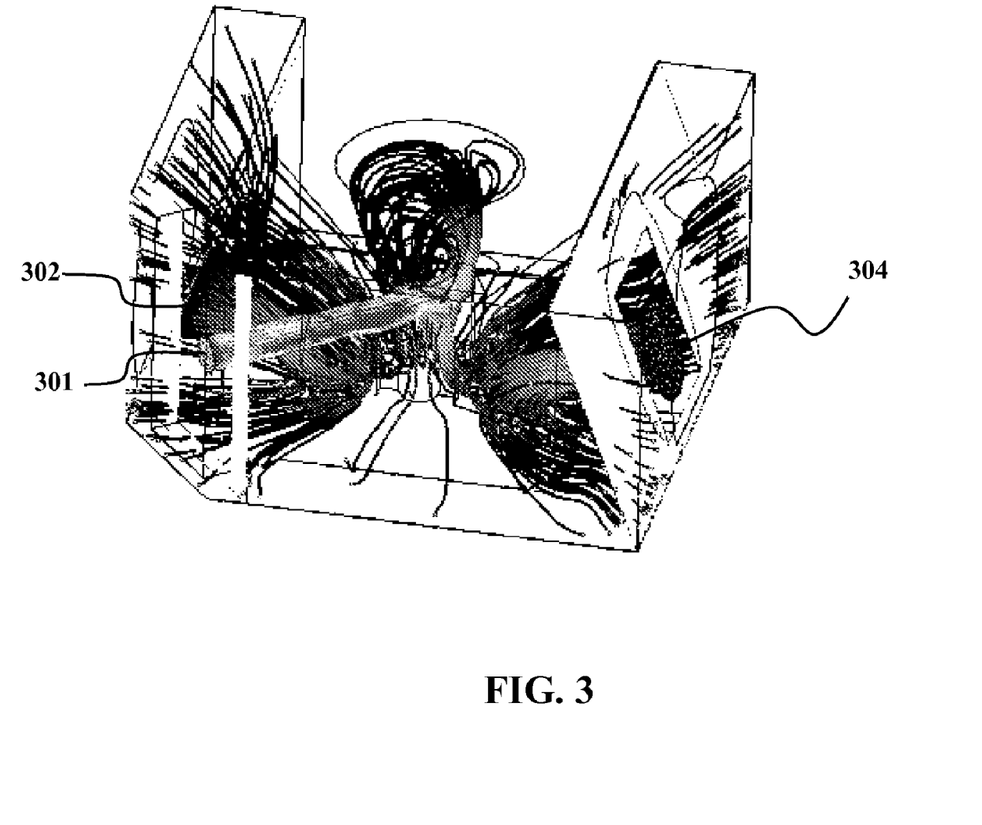
FIG. 3 illustrates a second flow pattern of nitrogen in a part of the gas purge system.

The flow rates of the purge gas at the inlets 108, 110 and 112 may be controlled separately, e.g., by valves coupled between the inlets and one or more gas sources. Purge gas flow rates through the input beam optics housing 102, collection optics housing 104 and gas purge manifold 106 may thus be independently controlled parameters. By adjusting the three purge gas flow rates at the three gas inlets 108, 110 and 112, the flow pattern between the BBSE and the wafer surface can be controlled. By way of example, FIG. 2 and FIG. 3 depict flow pattern simulation results for two cases with different flow rates. The flow patterns depict trajectories of many fluid particles. In FIG. 2, the flow rate of the normal purge from the purge gas manifold 106 is 0.4 L/min, and the flow rates for gas flows 202, 204 through the nosecones 122 and 124 are 4 L/min. In FIG. 3, the flow rate of a normal purge gas flow 301 through the purge gas manifold 106 is 0.5 L/min, and the flow rates for gas flows 302, 304 through each nosecone 122 and 124 are each 0.3 L/min. The flow patterns in FIG. 2 and FIG. 3 are totally different. Furthermore, in both cases the pattern of flow of purge gas over the substrate 116 is not radially symmetric.

In the purge gas system 100, a highest flow of purge gas is only needed for the purge system at an initial stage. At later stages, a lower flow may be used to maintain sufficient positive purge gas pressure to keep undesirable gases such as oxygen and water vapor out of the optical paths of the optical system used in conjunction with the purge gas system 100. The nitrogen flows 301,302, 304 may be adjusted so that nitrogen may be supplied where it is needed. In addition, when the system is not used, the nitrogen flow may be reduced, which reduces the use of purge gas while also reducing the recovery time. Finally, because purge gas flows through the housings 102, 104 and purge gas manifold 106, it is not necessary to enclose them in a chamber. Therefore, the gas purge system 100 is easier to assemble in manufacturing and optical components used with the purge gas system, e.g., an ellipsometer, may be more easily accessed for field service.

Embodiments of the present invention provide advantages over previous purge gas methods and systems. For example, U.S. Pat. No. 6,222,199 B1 describes a VUV spectroscopic ellipsometer (SE) that maintains a controlled ambient via housing the entire metrology apparatus inside a sealed container filled (purged) with purified nitrogen gas. This design has a purged volume that is significantly larger than the volume that encloses the VUV light path alone and must housing multiple components (e.g., optical elements, optical mounts, electrical components, electrical wiring, etc.), which do not need to be in the purged environment. In embodiments of the present invention, by contrast, only the optical beam paths are purged.

U.S. Pat. No. 6,813,026B2 describes a VUV optical metrology system that incorporates a gas-purge of the optical path that connects the illuminator, the sample and the detector. In this design, Nitrogen is purged from a cutout on a large area flat plat to the wafer surface, and creates a radially symmetric flow pattern. Unfortunately, such a design requires a relatively large purged volume between the flat plate and the wafer surface. As a result, purge times can be relatively slow with such a system. Embodiments of the present invention, by contrast, may use both a smaller purged volume and a non-radially symmetric flow patterns to achieve faster purge times.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A gas purge system, comprising:
    an input beam optics housing including a first nosecone, the input beam optics housing having a first gas flow path between a first gas inlet and an aperture in the first nose cone proximate a measurement position;
    a collection optics housing including a second nosecone, the collection beam optics housing having a second gas flow path between a second gas inlet and an aperture in the second nose cone proximate the measurement position; and
    a gas purge manifold disposed between the input beam optics housing and the collection optics housing, the gas purge manifold having third a gas flow path between a third gas inlet and an aperture in the gas manifold proximate the measurement position.

2. The gas purge system of claim 1, further comprising a dovetail plate adapted to mount the gas purge chamber, the input beam optics housing and the collection optics housing.

3. The gas purge system of claim 2, further comprising an objective mount adapted to mount an objective lens to the dovetail plate.

4. The gas purge system of claim 2, further comprising an objective sleeve adapted to seal the objective lens to the gas purge manifold.

5. The gas purge system of claim 1 wherein the first and/or second nosecone includes a truncated portion.

6. The gas purge system of claim 5 wherein the truncated portion includes a substantially flat surface oriented substantially parallel to a substrate.

7. The gas purge system of claim 1 wherein the measurement position is located proximate an intersection of an optical path through the input beam optics housing and an optical path through the collection optics housing.

8. The gas purge system of claim 1 wherein the measurement position is located at an intersection of an intersection of an optical path through the input beam optics housing, an optical path through the collection optics housing and a surface of a substrate.

9. The gas purge system of claim 1 wherein the aperture in the purge gas manifold is adapted to direct a flow of gas in a direction substantially normal to a surface of a substrate.

10. The gas purge system of claim 1 wherein the gas purge manifold is adapted to receive a focus lens and/or a collection lens.

11. The gas purge system of claim 10 wherein the focus lens and the collection lens are located inside the purge gas manifold.

12. The gas purge system of claim 1 wherein the gas purge manifold provides at least a portion of a light path for an optical component of an optical system.

13. The gas purge system of claim 12 wherein the light path is a light path for auto-focus light.

14. The gas purge system of claim 12 wherein the light path is a light path for an objective lens.

15. A method for purging a purge gas along a light path in a purge gas system, the purge gas system including a purge gas chamber, an input beam optics housing and a collection optics housing, the purge gas chamber including a purge gas manifold, the input beam optics housing including a first nosecone and the collection optics housing including a second nosecone, the method comprising:
    supplying a first flow of purge gas through the input beam optics housing;
    supplying a second flow of purge gas through the collection optics housing; and
    supplying a third flow of purge gas through the purge gas chamber;
    wherein the purge gas is delivered directly to a measurement position of a surface of a substrate through the purge gas manifold, the first nosecone and the second nose cone.

16. The method of claim 15 wherein supplying the first flow of purge gas through the input beam optics includes flowing the purge gas through an aperture in the first nosecone proximate the measurement position.

17. The method of claim 16 wherein supplying the second flow of purge gas through the collection optics includes flowing the purge gas through an aperture in the second nosecone proximate the measurement position.

18. The method of claim 17 wherein supplying the third flow of purge gas through the purge gas chamber includes flowing the purge gas through an aperture in the purge gas manifold proximate the measurement position.

19. The method of claim 15, further comprising independently controlling flow rates of the first, second and third flows of purge gas.

20. The method of claim 15 wherein supplying the first and second flows of purge gas includes directing the first flow of purge through the first nosecone at a first angle with respect to the surface of the substrate and directing the second flow of purge case through the second nosecone a second angle with respect to the surface of the substrate.

21. The method of claim 15 wherein supplying the third flow of purge gas through the purge gas manifold includes directing the third flow of purge gas in a normal direction with respect to the surface of the substrate.

22. The method of claim 15, further comprising reducing the first and/or second and/or third flows of purge gas after filling the purge gas chamber with the purge gas.

23. The method of claim 15 wherein a combined flow pattern resulting from the first, second and third flows of purge gas are not radially symmetric.

24. The method of claim 19 wherein a flow rate for the first, second or third flow of purge gas is between about 0.1 L/min and about 0.6 L/min.

25. A spectroscopic ellipsometer, comprising:
    an input beam optics housing including a first nosecone, the input beam optics housing having a path for gas flow between a first gas inlet and an aperture in the first nose cone proximate a measurement position;
    input beam optics disposed within the input beam optics housing;
    a collection optics housing including a second nosecone, the collection beam optics housing having a path for gas flow between a first gas inlet and an aperture in the second nose cone proximate the measurement position;
    collection optics disposed within the collection optics housing; and
    a gas purge manifold disposed between the input beam optics housing and the collection optics housing, the gas purge manifold having a path for gas flow between a third gas inlet and an aperture in the gas manifold proximate the measurement position.

26. The ellipsometer of claim 25 wherein the measurement position is located proximate an intersection of an optical path through the input beam optics and an optical path through the collection optics.

27. The ellipsometer of claim 25, further comprising a dovetail plate adapted to mount the gas purge manifold, the input optics housing and the collection optics housing.

28. The ellipsometer of claim 27, further comprising an objective mount adapted to mount an objective lens to the dovetail plate.

29. The ellipsometer of claim 25, further comprising an objective sleeve adapted to seal an objective lens to the gas purge manifold.

* * * * *